United States Patent
Harding et al.

(10) Patent No.: US 9,939,440 B2
(45) Date of Patent: Apr. 10, 2018

(54) ELECTROCHEMICAL ANALYTE DETECTION APPARATUS AND METHOD

(71) Applicant: AgaMatrix, Inc., Salem, NH (US)

(72) Inventors: Ian Harding, Wells (GB); Sridhar Iyengar, Salem, NH (US); Richard Williams, Somerville, MA (US)

(73) Assignee: AgaMatrix, Inc., Salem, NH (US)

(*) Notice: Subject to any disclaimer, the term of this patent is extended or adjusted under 35 U.S.C. 154(b) by 96 days.

(21) Appl. No.: 15/017,787

(22) Filed: Feb. 8, 2016

(65) Prior Publication Data

US 2016/0231321 A1 Aug. 11, 2016

Related U.S. Application Data

(63) Continuation of application No. 12/179,446, filed on Jul. 24, 2008, now abandoned.
(Continued)

(51) Int. Cl.
  *G01N 27/416* (2006.01)
  *G01N 33/573* (2006.01)
  (Continued)

(52) U.S. Cl.
  CPC .......... *G01N 33/573* (2013.01); *C12Q 1/001* (2013.01); *G01N 27/4166* (2013.01);
  (Continued)

(58) Field of Classification Search
  CPC .......... G01N 27/327–27/3278; G01N 33/53–33/5306; G01N 33/573–33/5735; G01N 2333/90; G01N 2333/902
  (Continued)

(56) References Cited

U.S. PATENT DOCUMENTS 3,654,090 A   4/1972  Schuurs et al.
4,169,012 A   9/1979  Dawson et al.
(Continued)

FOREIGN PATENT DOCUMENTS

CN   1463362 A    12/2003
EP   0150999 A2   8/1985
(Continued)

OTHER PUBLICATIONS

Rasmussen et al., Biophysical Characterization of the Cocaine Binding Pocket in the Serotonin Transporter Using a Fluorescent Cocaine Analogue as a Molecular Reporter, J. Biol. Chem., Feb. 16, 2001, pp. 4717-4723, vol. 276, No. 7.
(Continued)

*Primary Examiner* — Bach T Dinh
(74) *Attorney, Agent, or Firm* — Larson & Anderson, LLC

(57) ABSTRACT

A method and apparatus for electrochemical detection of analyte in a sample makes use of a binding interaction and relies on the discovery that asymmetric distribution of a redox enzyme between two electrodes that occurs when a redox enzyme-containing reagent is immobilized at the surface of one electrode can be detected as a chemical potential gradient arising from an asymmetry in the distribution of oxidized or reduced redox substrate. This chemical potential gradient can be detected potentiometrically by observing the potential difference between the electrodes in an open circuit, or amperometrically by observing the current flow between the electrodes when the circuit is closed. In both cases, the observation of asymmetry can be done without the application of an external potential or current to the electrodes.

15 Claims, 16 Drawing Sheets

Related U.S. Application Data

(60) Provisional application No. 60/952,099, filed on Jul. 26, 2007.

(51) Int. Cl.
   *C12Q 1/00* (2006.01)
   *G01N 33/543* (2006.01)

(52) U.S. Cl.
   CPC ..... *G01N 33/5438* (2013.01); *G01N 2333/90* (2013.01); *G01N 2333/902* (2013.01)

(58) Field of Classification Search
   USPC .............. 204/403.01–403.15; 205/777.5–778
   See application file for complete search history.

(56) References Cited

U.S. PATENT DOCUMENTS

| | | | |
|---|---|---|---|
| 4,642,285 A | 2/1987 | Halbert et al. | |
| 4,746,631 A | 5/1988 | Clagett | |
| 4,868,131 A | 9/1989 | Hiratsuka | |
| 4,943,522 A | 7/1990 | Elsinger et al. | |
| 5,122,244 A | 6/1992 | Hoenes et al. | |
| 5,149,630 A | 9/1992 | Forrest et al. | |
| 5,198,367 A | 3/1993 | Aizawa et al. | |
| 5,413,690 A | 5/1995 | Kost et al. | |
| 5,427,912 A | 6/1995 | Brown et al. | |
| 5,494,831 A | 2/1996 | Kindler | |
| 5,618,926 A | 4/1997 | Salamone et al. | |
| 5,656,503 A | 8/1997 | May et al. | |
| 5,677,132 A | 10/1997 | Strahilevitz | |
| 5,708,247 A | 1/1998 | McAleer et al. | |
| 5,712,172 A | 1/1998 | Huang et al. | |
| 5,766,961 A | 6/1998 | Pawlak et al. | |
| 5,942,388 A * | 8/1999 | Willner | C12Q 1/003 204/193 |
| 5,981,298 A | 11/1999 | Chudzik et al. | |
| 5,989,921 A | 11/1999 | Charlton et al. | |
| 6,020,209 A | 2/2000 | Narang et al. | |
| 6,110,696 A | 8/2000 | Brown et al. | |
| 6,478,938 B1 | 11/2002 | Paek et al. | |
| 6,635,434 B1 | 10/2003 | Jakobsen et al. | |
| 6,806,359 B1 | 10/2004 | Evans et al. | |
| 7,214,511 B1 | 5/2007 | Evans et al. | |
| 7,220,842 B2 | 5/2007 | Zheng et al. | |
| 2002/0090738 A1 | 7/2002 | Cozzette et al. | |
| 2003/0143598 A1 | 7/2003 | Garimella et al. | |
| 2003/0175828 A1 | 9/2003 | Watanabe et al. | |
| 2004/0245101 A1* | 12/2004 | Willner | C12Q 1/004 204/403.01 |
| 2005/0130208 A1 | 6/2005 | Stojanovic et al. | |
| 2005/0258035 A1 | 11/2005 | Harding et al. | |
| 2005/0265094 A1 | 12/2005 | Harding et al. | |
| 2006/0030028 A1 | 2/2006 | Nakaminami et al. | |
| 2006/0160100 A1* | 7/2006 | Gao | B82Y 15/00 435/6.11 |

FOREIGN PATENT DOCUMENTS

| | | |
|---|---|---|
| EP | 0640832 A2 | 3/1995 |
| EP | 0402126 B1 | 4/1996 |
| WO | 9503543 A1 | 2/1995 |
| WO | 2005022143 A2 | 3/2005 |

OTHER PUBLICATIONS

Mir et al., "Different Strategies to Develop an Electrochemical Thrombin Aptasensor", Electrochemical Communications, Mar. 2006, pp. 505-511, vol. 8, Issue 3, Abstract only.
http://www.domantis.com/, Domain Antibodies, 2008.
Xu, et al., Preparation and Application of AFP Immunosensor with Methylene Blue as Mediator, Physical Testing and chemical Analysis Part B: Chemical Analysis, Dec. 18, 2006, pp. 973-976, vol. 42, Issue 12 (English translation of abstract only).

\* cited by examiner

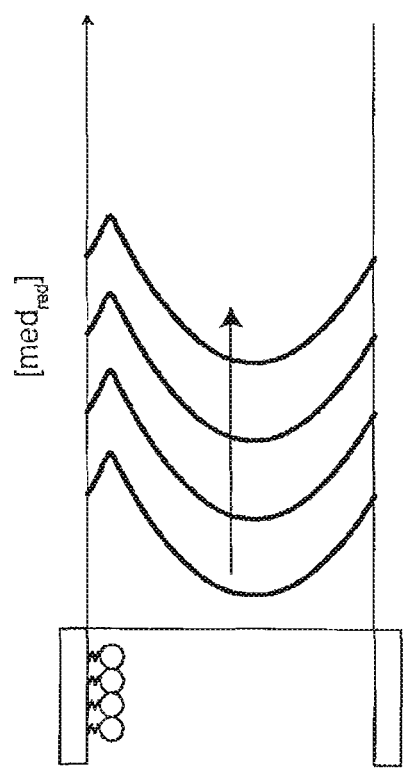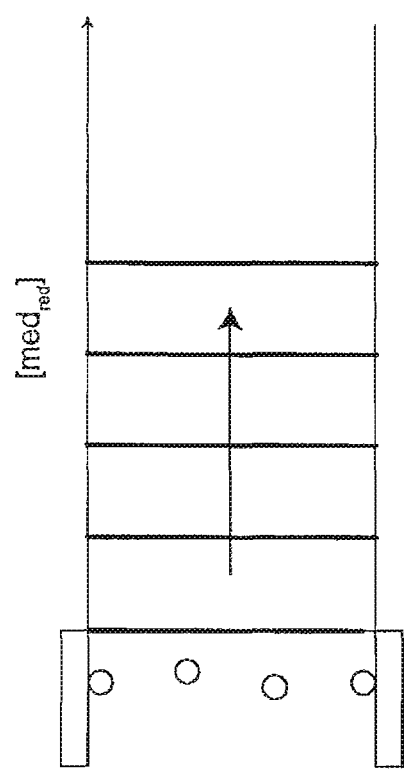
Asymmetric Enzyme Distribution
I > 0
Symmetric Enzyme Distribution
I = 0
Fig. 2A
Fig. 2B

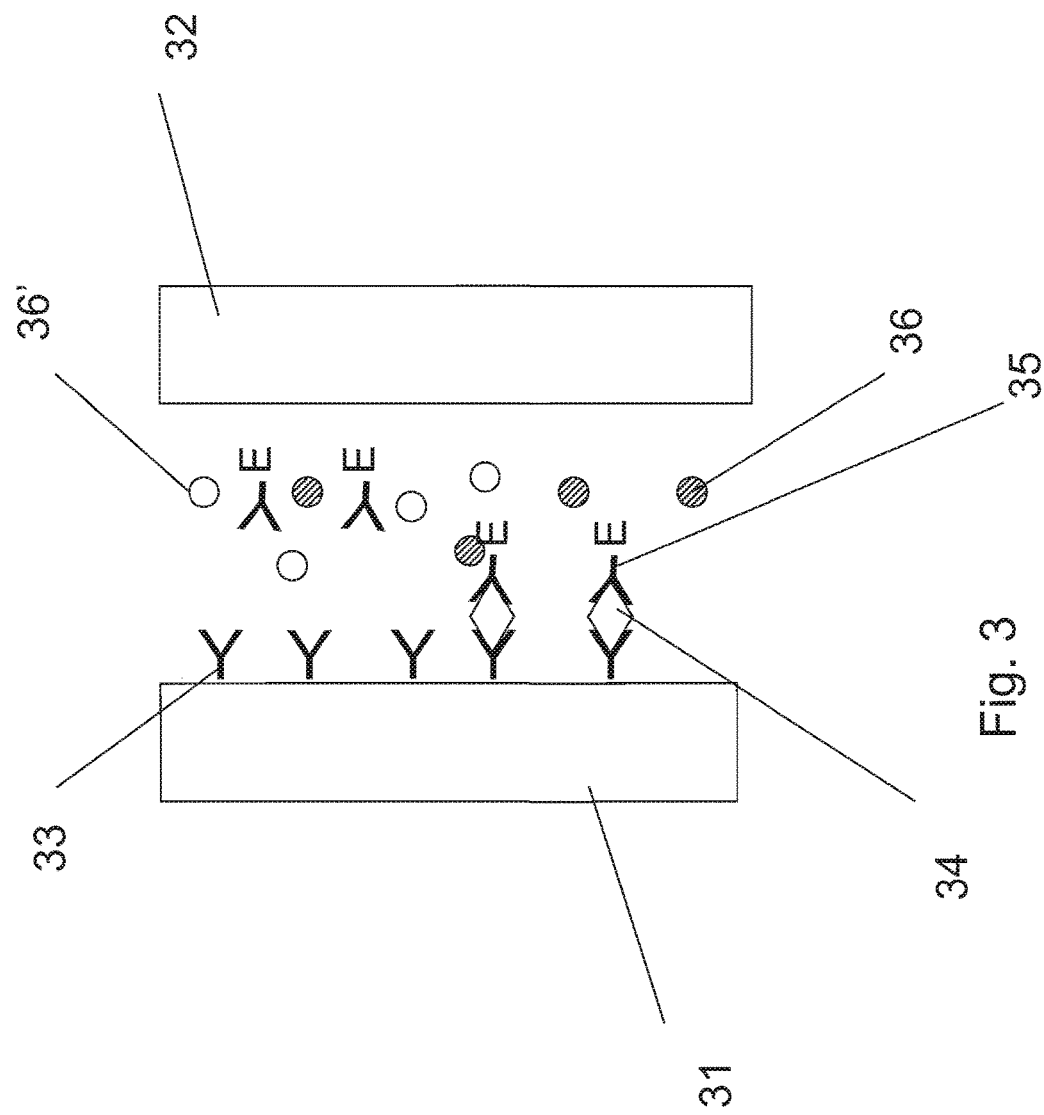

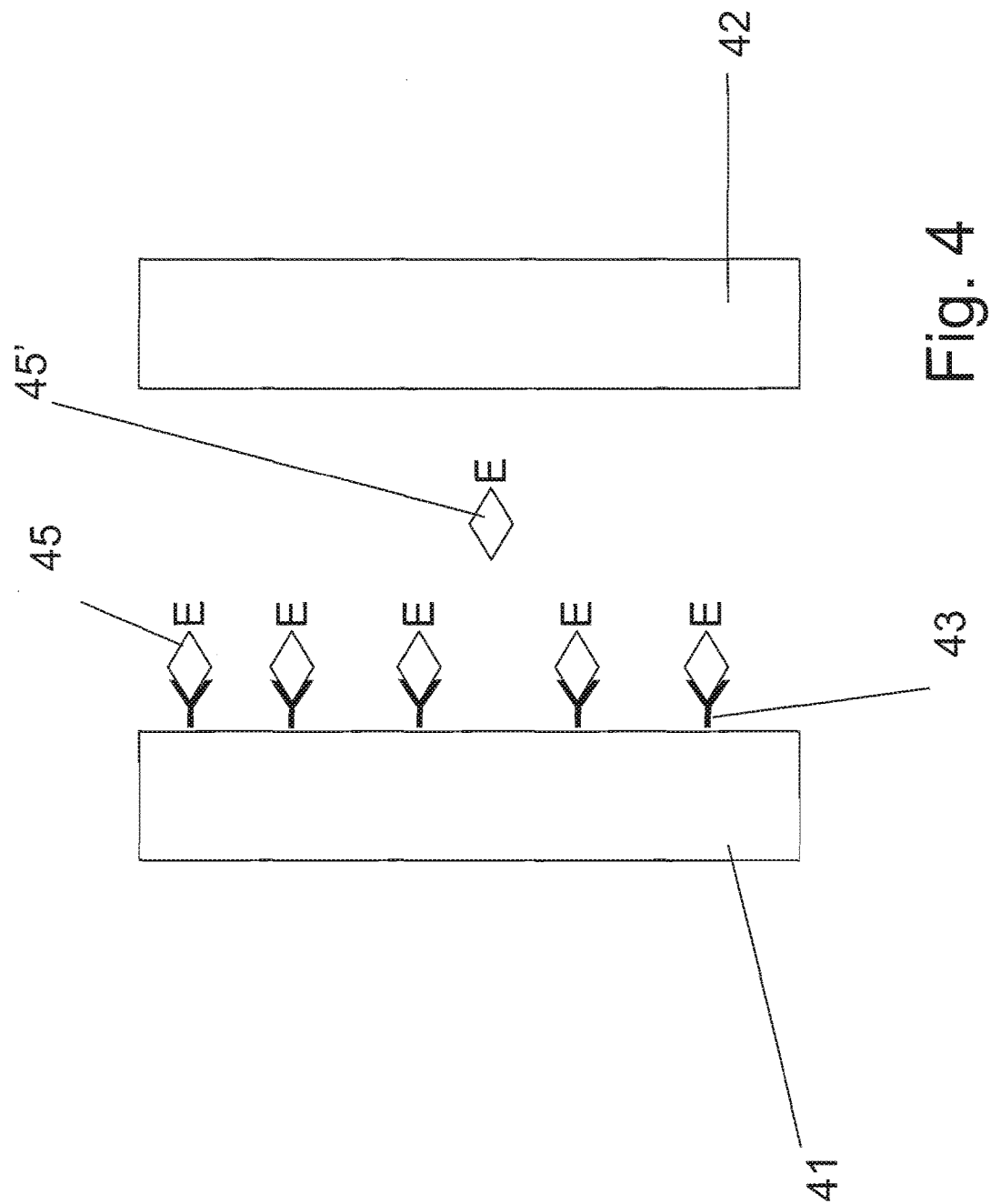

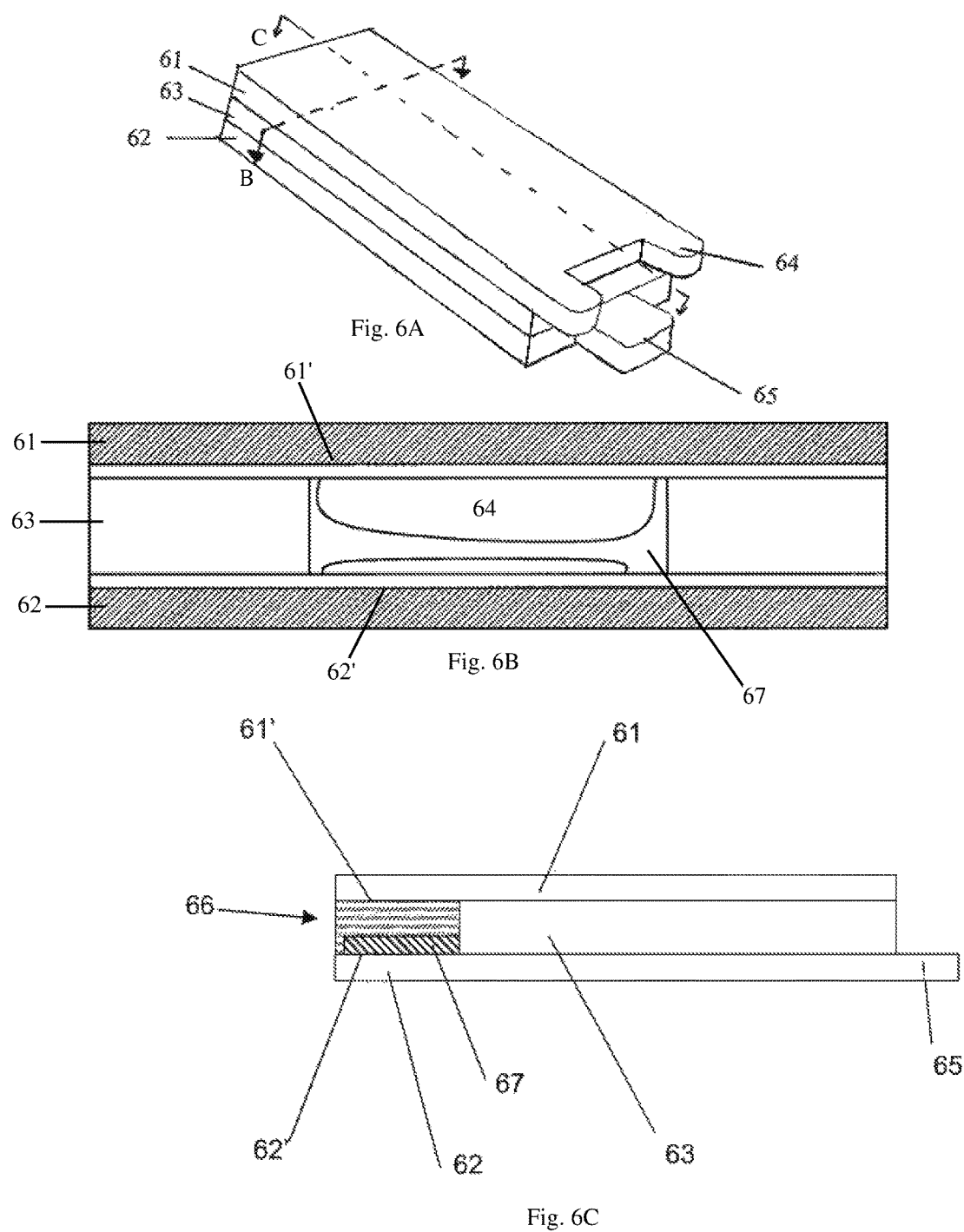

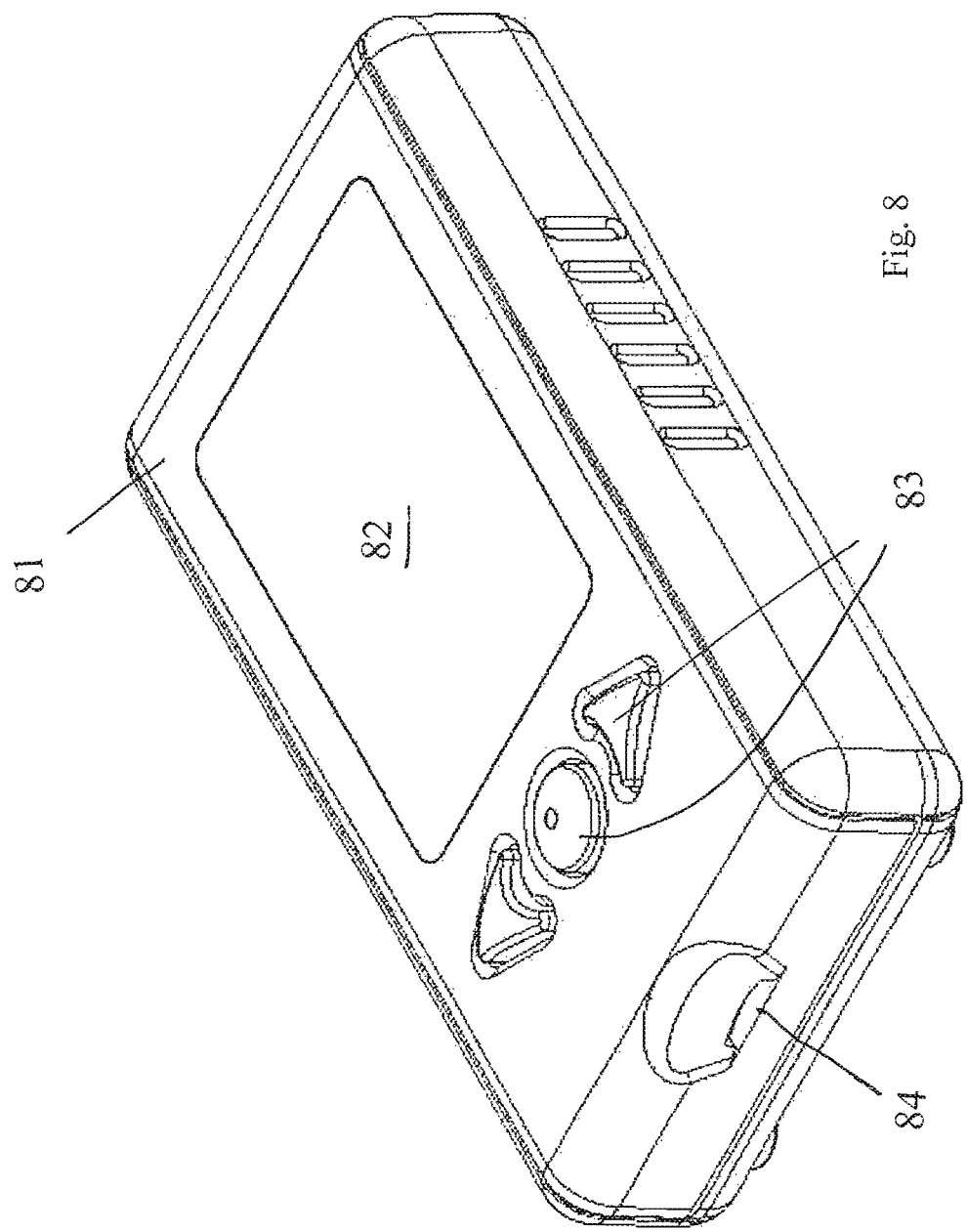

Fig. 10 : Effect of ratio of enzyme activities at the two electrodes on potentiometric signal Fig. 11 : Effect of ratio of enzyme activities at the two electrodes on amperometric signal Fig. 12 : Peak potential difference correlates with ratio of electrode enzyme activities Fig. 13: Peak current correlates with ratio of electrode enzyme activities

ELECTROCHEMICAL ANALYTE DETECTION APPARATUS AND METHOD

This application claims the benefit of U.S. Provisional Application No. 60/952,099 filed Jul. 26, 2007, which application is incorporated herein by reference for all purposes.

BACKGROUND OF THE INVENTION

This application relates to an apparatus and method for electrochemical detection of an analyte in a sample. The invention utilizes a specific binding relationship between the analyte and at least one reagent provided in the apparatus as a means for detecting the analyte.

Analysis methods in which specific binding between an analyte and a reagent forms the basis for the assay are known. For example, in enzyme-linked immunoassay (EIA or ELISA) procedures, a sandwich is formed between an immobilized antibody and a mobile enzyme-antibody reagent when analyte is present through the interaction of the analyte with the antibody components. This results in the immobilization of the enzyme. The subsequent detection of immobilized enzyme is therefore indicative the presence of analyte in a test solution. (See U.S. Pat. Nos. 3,654,090, 4,169,012, and 4,642,285) Similar sandwich assays are used in chromatographic immunoassays where a colored tag (for example a colored latex bead) on the mobile reagent becomes trapped on a substrate at a defined location to produce a pattern that indicates the presence of analyte in a sample. (See U.S. Pat. Nos. 4,943,522, 5,656,503, 5,712,172 and 5,766,961) Analysis methods that depend on specific binding between an analyte and a reagent may also take the form of competition assays, in which the formation of a complex involving a labeled reagent is inhibited in the presence of analyte in an analyte-concentration dependent manner (See U.S. Pat. Nos. 4,868,131, 5,981,298 and 5,989,921), or displacement assays in which a pre-existing complex involving a labeled reagent is disrupted in the presence of analyte in an analyte-concentration dependent manner. (See U.S. Pat. Nos. 4,746,631 and 6,020,209).

Immunoassays in which detection of the analyte depends on an electrochemical measurement are also known. U.S. Pat. No. 5,149,630 discloses an assay in which the extent to which the transfer of electrons between an enzyme substrate and an electrode, associated with the substrate reaction, is perturbed by complex formation or by displacement of any ligand complex relative to unbound enzyme-labelled component. This determination is made in the presence of an applied potential. An applied potential is also used to measure current in the assay device disclosed in U.S. Pat. Nos. 5,198,367, 5,427,912. U.S. Pat. No. 5,494,831 discloses the application of a current and the measurement of changes in impedance that result in binding.

SUMMARY OF THE INVENTION

The present invention provides a new method and apparatus for electrochemical detection of analyte in a sample that makes use of a binding interaction. The invention relies on the discovery that asymmetric distribution of a redox enzyme between two electrodes that occurs when a redox enzyme-containing reagent is immobilized at the surface of one electrode can be detected as a chemical potential gradient arising from an asymmetry in the distribution of oxidized or reduced redox substrate. This chemical potential gradient can be detected potentiometrically by observing the potential difference between the electrodes in an open circuit, or amperometrically by observing the current flow between the electrodes when the circuit is closed. In both cases, the observation of asymmetry can be done without the application of an external potential or current to the electrodes.

In a first embodiment of the invention, a sandwich type assay is utilized. In this embodiment, a sample to be tested for analyte is introduced to a test cell in the presence of a mobile test reagent. The test cell comprises a first and a second electrode. The first electrode has immobilized on the surface thereof an immobilized test reagent. The mobile test reagent comprises an analyte-binding portion and a redox enzyme portion, and the immobilized test reagent comprises an analyte binding portion. If analyte is present in the sample in the test cell, at least a portion of the mobile test reagent becomes immobilized on the first electrode thereby creating an asymmetry in redox enzyme concentration between the first and second electrodes when analyte is present. A redox substrate for the redox enzyme in the test cell is also supplied. The redox substrate is acted upon (oxidized or reduced) by the redox enzyme. If there is an asymmetry in redox enzyme concentration between the first and second electrodes (i.e. when analyte is present in the sample), this results in a chemical potential gradient between the first and second electrodes. This chemical potential gradient is detected to determine analyte in the sample. In this embodiment, the greater the asymmetry and the resulting potential gradient, the greater the amount of analyte in the sample.

In a second embodiment of the invention, a competition or displacement type of assay is utilized. In this assay, the redox enzyme is coupled to analyte or an analog of the analyte that can bind to a common immobilized test reagent. Optionally, the redox enzyme is provided already bound to the electrode via the immobilized test reagent. When sample is added, analyte present in the sample will compete with the redox enzyme for the binding sites provided by the immobilized test reagent resulting in a reduction in the amount of asymmetry that would occur is all of the binding sites were occupied by redox enzyme.

BRIEF DESCRIPTION OF THE DRAWINGS

FIGS. 2A and B illustrate the determination of asymmetric enzyme distribution at two electrodes using amperometry.

FIG. 3 shows a sandwich assay format useful in the present invention.

FIGS. 4 and 5 shows competition/displacement assay format useful in the present invention.

FIGS. 6A-C shows construction of a test cell with facing electrodes.

FIG. 8 shows an external view of a meter in accordance with the invention.

DETAILED DESCRIPTION OF THE INVENTION

I. Definitions

Figures 1A, 1B:
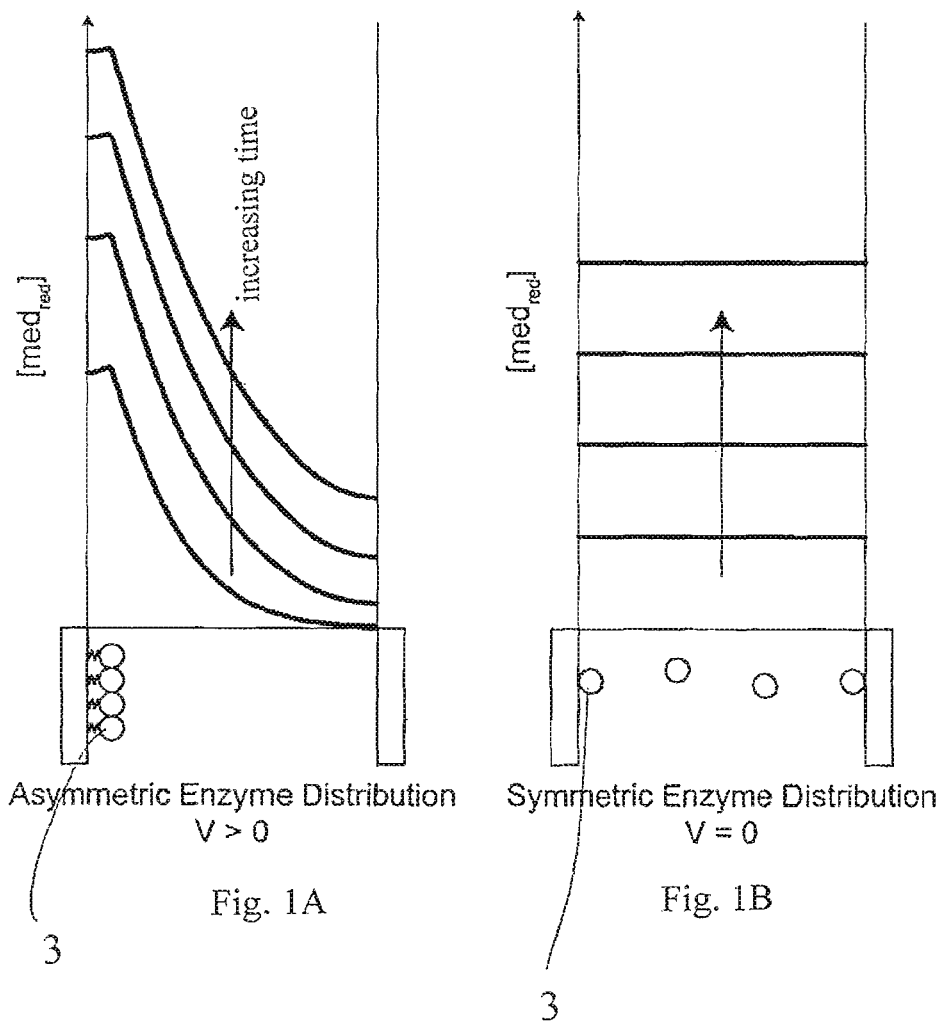
FIGS. 1A and B show schematic representations of reduced mediator distribution between two electrodes when redox enzyme distribution is asymmetric (FIG. 1A) or symmetric (FIG. 1B).

As used in the specification and claims of this application, the following definitions should be applied:

(a) "analyte" refers to a material of interest that may be present in a sample. Analytes that are detectable in the present invention are those that can be associated in a specific-binding interaction with at least one other reagent to that they can participate in a sandwich, competition or displacement assay configuration as described herein. Examples of analytes include antigens or haptens such as peptides (for example hormones), proteins (for example, enzymes), drugs, pesticides, microorganisms, antibodies, and nucleic acids that can participate in sequence specific hybridization reactions with a complementary sequence.

(b) "analyte-specific enzyme component" or reagent refers to a reagent that includes both an analyte-binding portion and a redox enzyme portion. An analyte-specific enzyme component is suitably used as a mobile reagent.

(c) "determination of an analyte" refers to qualitative, semi-quantitative and quantitative processes for evaluating a sample. In a qualitative evaluation, a result indicates whether or not analyte was detected in the sample. In a semi-quantitative evaluation, the result indicates whether or not analyte is present above some pre-defined threshold. In a quantitative evaluation, the result is a numerical indication of the amount of analyte present.

(d) the term "redox enzyme" refers to an enzyme that oxidizes or reduces a substrate. Such enzymes may generally be known as oxidases, peroxidases, reductases, or dehydrogenases. Enzymes such as glucose oxidase, and various peroxidases are commonly used in the analytical devices, and therefore the preparation of these enzymes in stable form is well known.

(e) the term "redox substrate" refers to a compound or combination of compounds that interact with the redox enzyme to produce a chemical potential gradient. In some cases, the enzyme substrate may directly produce a redox active species sufficient to create the chemical potential gradient. In others, a secondary compound may be needed. For example, in the case of glucose oxidase, the interaction with glucose to produce gluconolactone and reduced enzyme produces the chemical potential gradient when the reduced enzyme is oxidized by a mediator compound, which is the actual redox active species in the chemical potential gradient. Thus, in this case the "redox substrate" is the combination of the substrate compound glucose and the mediator compound.

(f) the term "chemical potential gradient" refers to a concentration gradient of a redox active species. It will be appreciated that more rigorously, the potential gradient arises from a gradient in the ratio of reduced to oxidized species between the electrodes, however, the idea of a concentration gradient of one species is more easily visualized and is therefore used here. When such a gradient is present between two electrodes, a potential difference is detectable if the circuit is opened, and a current will flow until the gradient dissipates when the circuit is closed. It will be appreciated that the chemical potential gradient is transient in the devices of the invention, and that the distribution of the redox active species will even out over time, when new redox active species stops being created. The term "chemical potential gradient" as used herein refers only to this transient gradient that arises from the asymmetry of the distribution of redox enzyme and not to any potential gradient that arises from the application of a potential difference or current flow between the electrodes.

(g) the phrase "detecting the chemical potential gradient between the first and second electrodes" refers to the detection of the chemical potential gradient in either an open or a closed circuit, using either potentiometric or amperometric measurements.

(h) the terms "enzyme activity" and "enzyme concentration" are used as equivalent terms herein, although it will be appreciated that in ordinary usage they may have different meanings. Activity of an enzyme provides a quantitative measure of the catalytic capability of an enzyme. This depends not only on the physical amount of the enzyme present in the volume (i.e. the concentration), but also on the conditions which affect the catalytic efficiency of the enzyme. The present invention actually measures asymmetry in enzyme activity, since the presence of inactive enzyme will not produce an asymmetry in redox substrate. However, since it is desirable to control the quality of the enzyme and the conditions, this is in effect also a measurement of asymmetry in enzyme concentration.

(i) the term "immobilized on the first electrode" refers to immobilization directly or indirectly on the surface of the electrode, provided that the material immobilized becomes immobilized in volume associated with the first electrode and closer to the first electrode than the second electrode. For example, in the case of the formation of an electrode-antibody-analyte-antibody-enzyme sandwich, the enzyme is considered to be "immobilized on" the electrode even though there are several intervening moieties in the sandwich.

(j) the term "immobilized test reagent" refers to the component of a sandwich or competition/displacement reaction that is associated with an electrode when performing the assay of the invention. Immobilization may be through the formation of a chemical bond (covalent or non-covalent) between the immobilized test reagent and the surface of the electrode, or it may be a physical association as through the placement of the immobilized test reagent within a gel or membrane disposed on the surface of the electrode. The immobilized test reagent comprises a binding moiety which interacts with analyte to produce a change in the distribution of the redox enzyme (as part of the analyte-binding enzyme component) when analyte is present in a sample. In some embodiments, the immobilized reagent will be immobilized during initial manufacture of the test apparatus. In other embodiments, immobilization will occur in situ after addition of the sample. Thus, the term immobilized test reagent refers to any circumstance in which the structure:

electrode-(link)$_n$-reagent with binding site for analyte is obtained, where n is 0 or an integer of 1 or greater. The latter option allows production of one set of generic devices in which the linking agent is not analyte specific, with the addition of reagent that binds to the link and the analyte for any given analyte-specific test. This additional reagent could be added to the test strip at manufacture, or to the sample prior to application to the test device.

II. Theory of the Invention

For convenience, the theoretical basis for the invention will be discussed in the context of glucose oxidase as the redox enzyme and a combination of glucose and a mediator as the redox substrate. Nothing in this discussion should be taken as an indication, however, that the invention is limited to use with these materials.

In common glucose measurement systems, enzyme present in the sample cell oxidizes glucose to gluconolactone, and the enzyme is reduced. Oxidized mediator (for example ferricyanide) reacts with the reduced enzyme to regenerate the oxidized form of the enzyme, and produce reduced mediator. This process continues until either glucose or oxidized mediator is exhausted. If the enzyme is distributed asymmetrically within the sample cell, then the production of reduced mediator is also asymmetric, and the resulting asymmetry in the distribution of reduced mediator persists for a period of time (determined by diffusion parameters) even after exhaustion of the limiting reagent.

When reduced mediator is present in a solution between two electrodes, the potential difference between the two electrodes is given by the Nernst equation $$E = \frac{RT}{F} \times \log\left(\frac{[med_{red}]_{electrode\,1}}{[med_{ox}]_{electrode\,1}} \times \frac{[med_{ox}]_{electrode\,2}}{[med_{red}]_{electrode\,2}}\right)$$

where E is the potential difference between electrodes 1 and 2, R is the gas constant, T is the absolute temperature and F is the Faraday constant. When there is no difference in the concentration of reduced mediator at the two electrodes (i.e. no chemical potential gradient) because there is no asymmetry, the mediator terms reduce to 1, log 1=0, and so the potential difference is 0. As the asymmetry increases, the potential difference increases. Furthermore, if the system is designed such that the oxidized mediator concentration at the time of measurement is large compared to the amount of reduced mediator (either due to a large excess of oxidized mediator initially or rapid taking of the measurement or both) then the oxidized mediator concentration at the two electrodes is essentially equal, and the equation can be simplified to:

$$E = \frac{RT}{F} \times \log\left(\frac{[med_{red}]_{electrode\,1}}{[med_{red}]_{electrode\,2}}\right)$$

FIGS. 1A and B show schematic representations of reduced mediator distribution between two electrodes (1, 2) when redox enzyme distribution is asymmetric (FIG. 1A) or symmetric (FIG. 1B). The equations above can be used to quantitate the ratio of concentrations of enzyme at two electrodes 1 and 2 using potentiometry. The two electrodes are connected in open circuit, and the potential difference between them is measured. If enzyme 3 is more active or concentrated at one electrode than the other (i.e., it has an asymmetric distribution as shown in FIG. 1A), the concentration of reduced mediator will be higher at that electrode than the other, giving rise to a electrical potential difference between the electrodes. If equal activity or concentrations of enzyme are present at both electrodes (i.e., it has a symmetric distribution as shown in FIG. 1B), the concentration of reduced mediator at each electrode will be equal, and the electrodes will be at equal electrical potential and the measured potential difference will be 0.

If, instead of potentiometry, the electrodes are connected in short-circuit, the asymmetric distribution of enzyme activity will result in an asymmetric distribution of reduced mediator, that can be observed by following current when the potential difference between the electrodes is forced to zero by closing the circuit between them. If reduced mediator is generated by enzyme activity and diffuses to an electrode, current will flow and sufficient mediator will be reoxidized, such that the reduced mediator concentration is equal at both electrodes. The current flow will be proportional to the difference in flux of reduced mediator to the two electrodes.

FIGS. 2A and B illustrate the use of these principles to quantify the ratio of concentrations of enzyme at two electrodes, using amperometry. The two electrodes are connected in short circuit, and the current flowing between them is measured. As electrical potential difference between the electrodes is constrained to zero, mediator will be reduced or oxidized at the electrodes when necessary to maintain an equal chemical potential at each electrode. As reduced mediator is oxidized at one electrode, current will flow and an equivalent quantity of oxidized mediator will be reduced at the other electrode. If the enzyme activity at each electrode is equal, no electron transfer will be necessary to keep the chemical potentials balanced, so no current will flow. If more enzyme activity is present at one electrode than the other, reduced mediator will be consumed at that electrode and produced at the other electrode to maintain a balanced chemical potential, and current will flow.

III. Practical Applications

The theory of the present invention is applicable to the practical application of determining analytes in a sample. This can be done in various binding formats. In general, two analyte-specific chemical components are utilized, and these are selected in to correspond to the analyte to be determined. In general, it is desired to have at least one of the components (generally the analyte-receptor) be highly specific for the analyte while the other component can be less specific in its binding. Various non-limiting combinations are set forth in Table 1.

| Analyte | Analyte receptor | binding component of Analyte-specific enzyme |
|---|---|---|
| disease-specific antibody, for example an antibody to influenza, disease causing organism | disease associated-antigen, such as peptide epitope found on an influenza of interest, aptamers | antibody that recognizes human antibodies, aptamers |
| amplified nucleic acid sequence including a suspected target and a known primer | nucleic acid complementary to the suspected target | nucleic acid sequence complementary to the known primer |
| hormone | hormone receptor, apatamer or antibody | hormone receptor, apatamer or antibody |
| drug | drug receptor, aptamer or | hormone receptor, |

-continued

| Analyte | Analyte receptor | binding component of Analyte-specific enzyme |
|---------|------------------|----------------------------------------------|
| pesticides | antibody pesticide binding proteins, aptamers. antibodies to pesticides | apatamer or antibody pesticide binding proteins, apatmers antibodies that recognize the antibodies to pesticides |

As will be understood in the art, the "antibody" incorporated in the device can be a complete antibody such as an immunoglobulin, or it may be a engineered binding portion of an antibody such as a single-chain antibody (scFv) or Domain Antibodies (dAb) as described at www.domantis.com. Immunoassays for drugs are described in U.S. Pat. Nos. 7,220,842, 5,677,132 and 5,618,926. Immunoassays for pesticides and pesticide degradation products are described in U.S. Pat. No. 6,635,434. Drug and hormone receptors may be native hormone receptors, or they may be engineered species with similar binding properties as are known in the art. (See U.S. Pat. Nos. 7,214,511, and 6,806,359, Rasmussen et al, J. Biol. Chem., Vol. 276, Issue 7, 4717-4723, Feb. 16, 2001). US Patent Publication 20050130208 discloses a cocaine-specific aptamer that could be used as a binding portion of an analyte-specific enzyme component or as an immobilized test reagent. Other aptmers are listed on the database of the Ellington research group at http://aptamer.icmb.utexas.edu/. Enzyme-aptamer coupling has been described by Mir et al. "Different Strategies To Develop an Electrochemical Thrombin Aptasensor." *Electrochemical Communication* 8 (2006): 505-511.

The components of the reaction are combined in such a way that they result in a difference in distribution symmetry of the redox enzyme that is dependent on the presence or absence of analyte in a sample. Various device formats can achieve this result.

A. Sandwich Format

FIG. 3 shows two electrodes 31 and 32. Electrode 31 has analyte-specific receptors 33 immobilized on the interior surface thereof. Analyte 34 associates with the analyte specific receptors 33. Also present is an analyte-specific enzyme reagent 35 which associates with analyte in such as way that the activity of the enzyme is maintained in the bound and the unbound state, and a redox substrate 36, 36'. Capture of the analyte-specific enzyme reagent 35 occurs at the surface of electrode 31 when analyte 34 is present because of the formation of receptor 33-analyte 34-analyte-specific enzyme species 35 sandwich. The activity of the enzyme results in an increased concentration of one form of the redox substrate (in the case of FIG. 3, of form 36) near electrode 31, and hence a detectable chemical potential gradient whose magnitude is related to the amount of analyte develops. When the analyte is not present, the sandwich does not form and thus no detectable chemical potential gradient is produced.

B. Competition/Displacement Format

Figure 5:
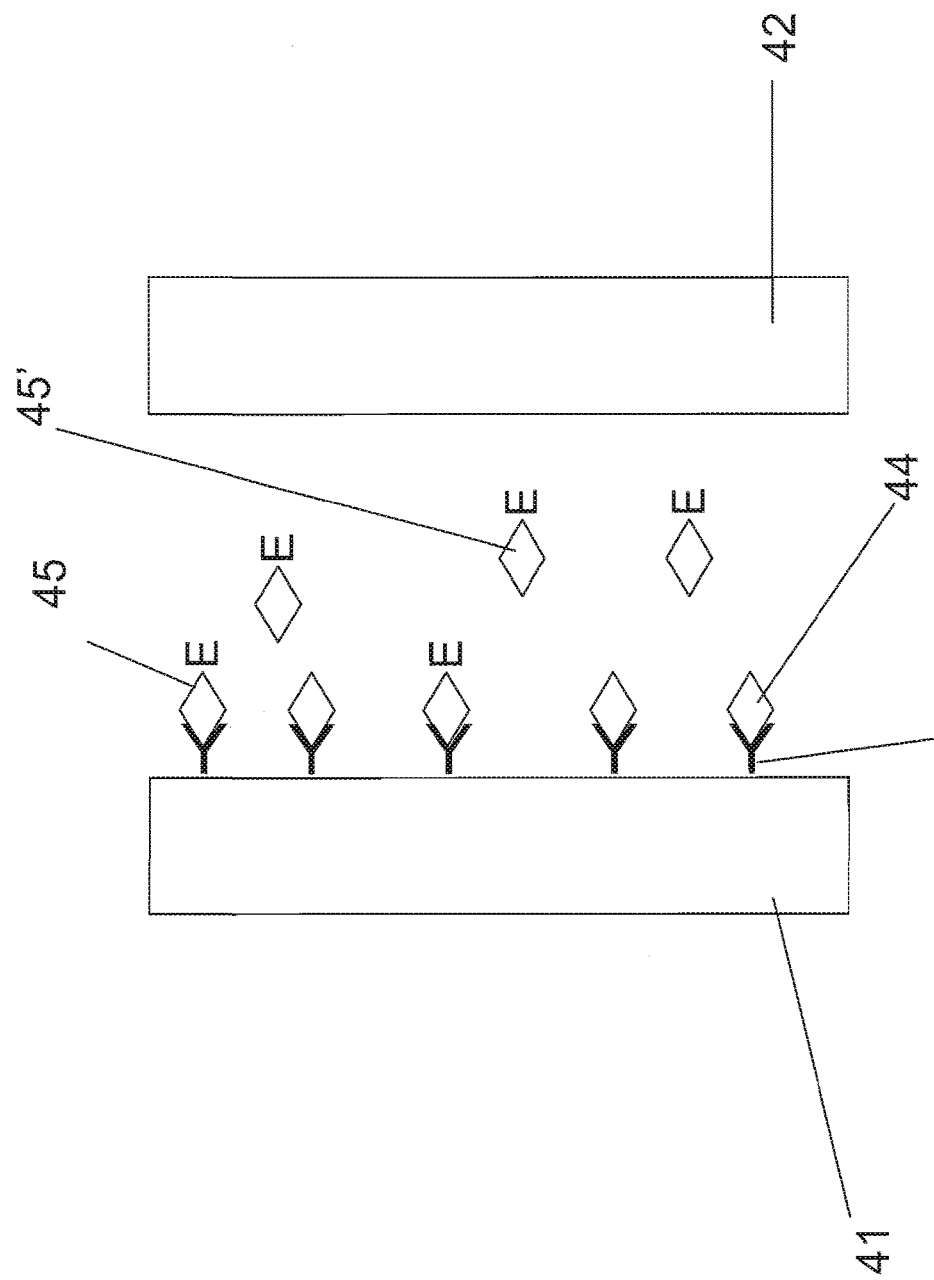

FIGS. 4 and 5 show a competition format for an assay device in accordance with the invention. The sample cell is defined by two electrodes 41, 42. Electrode 41 has analyte-receptors 43 disposed thereon. The redox enzyme 45 comprises the enzyme coupled to an analyte or an analyte mimetic. In the absence of analyte, as shown in FIG. 4, redox enzyme 45 is coupled to analyte receptor 43, resulting in an asymmetry in the distribution of the redox enzyme. Additional redox enzyme 45' may be present in the bulk of the sample depending on the amount of redox enzyme, analyte receptors and the affinity of the analyte receptors for the redox enzyme. As shown in FIG. 5, when analyte 44 is present, it competes with redox enzyme 45 for the analyte receptor 43, resulting in the displacement of at least some of the redox enzyme 45 from the analyte receptors 43, creating a less asymmetric distribution of the redox enzyme and thus the ability to determine analyte in a sample.

C. Device Construction—Sample Cell with Facing Electrodes

FIGS. 6A-C show a sample cell for a device in accordance with the invention, constructed using facing electrodes. The device is formed from a top layer 61 and bottom layer 62, each having a conductive surface (61', 62') facing the interior of the device, and an insulating spacer layer 63. Contacts 64 and 65 extend from the top layer 61 and bottom layer 62 to allow contact with the conductive surfaces for either potentiometric or amperometric measurements. As shown in FIG. 6B, the conductive layer 63 has an opening therein that together with the facing conductive surfaces 61' and 62' defines a sample cell. This sample cell is open to the exterior for introduction of sample, for example through an opening 66 at the end device as shown in FIG. 6C. Various structures for forming cells of this type, with multiple openings and/or vent holes are known in the art for example as the particular design of the cell is not critical to the practicing of the present invention. Similarly, other designs for connectors are known, and this also is not critical to the practicing of the present invention.

In an embodiment of the device of the invention, one of the conductive surfaces (61' or 62') has the analyte receptor (immobilized test reagent) disposed thereon. The remainder of the reagents for determination of analyte may be disposed within the sample cell as a dried reagent layer 67, or may be added to the sample prior to introduction to the sample cell.

The sample cell portion as shown in FIGS. 6A-C is generally constructed as a single use, disposable component.

D. Device Construction—Side-by-Side Electrodes

Figure 7A:
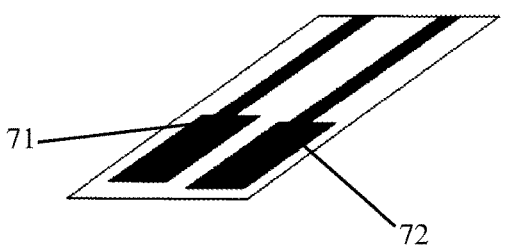
FIGS. 7A-C show examples of side-by-side electrode configurations.
Figure 7B:
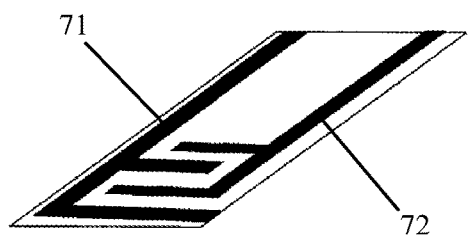
Figure 7C:
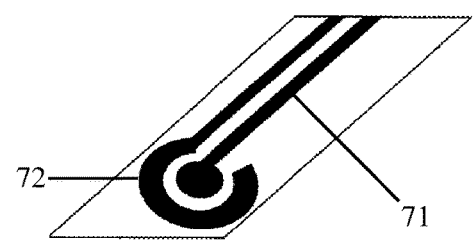

In addition to facing electrodes as discussed above, the first and electrodes may be disposed on the same surface within the sample cell. This configuration is referred to herein as side-by-side electrodes. FIGS. 7A-C show non-limiting examples of configurations that can be used for side-by-side configurations, including parallel strips (FIG. 7A), interdigitated strips (7B) and concentric rings (FIG. 7C). In each case, asymmetry in redox enzyme distribution between one electrode 71 and the other electrode 72 results in a measurable chemical potential gradient between the two electrodes.

The sample cell portions as shown in FIGS. 7A-C are generally constructed as a single use, disposable component.

E. Device Construction—Communication of Results

In addition to the sample cell, the device of the invention has a means for communicating the observed potential or current to a user in a meaningful way indicative of the determination of analyte. This can range from a simple qualitative result (analyte present or not present), or to a specific numerical value for the amount of analyte. The sophistication of the communication means varies accordingly.

In one embodiment of the invention, to provide a qualitative result, the device may have at a visible location a spot of a material that changes color in response to the passage of current or the application of the potential difference created by an asymmetry above a threshold level. In this case, the device does not need a separate meter portion, and may be simply a disposable test strip with an indicator spot on the outside.

More commonly, the sample cell will be contained within a disposable test strip that is inserted into a reusable meter. The meter will contain the electronics for measuring the potential difference or current at a defined period of time after introduction of a sample or test strip, and for conversion of the measured value to a displayed value. This conversion may make use of a look-up table that converts specific value of current or potential to values of analyte depending on the calibration values for the specific device geometry and analyte.

FIG. 8 shows an external view of a meter in accordance with the invention. As shown, the meter has a housing 81 having a display 82 and one or more control interfaces 83 (for example power buttons, or scroll wheels etc). The housing has a slot 84 for receiving a test device. Internal to the housing 81 is circuitry for applying a potential or current to the electrodes of the test device when a sample is applied. This may be done following an initialization signal from a user, or following an automated detection of test device insertion and sample application.

Figure 9:
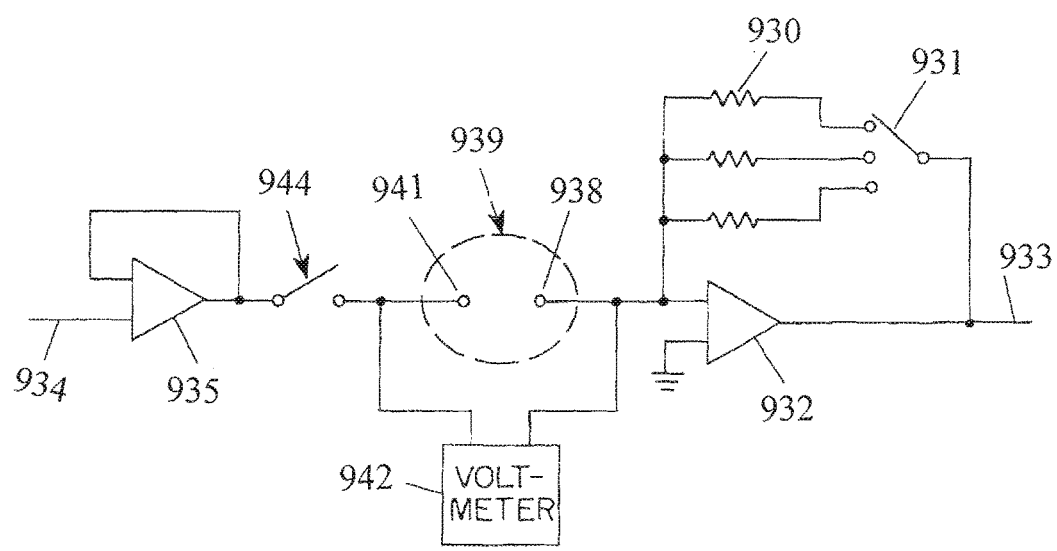
FIG. 9 shows a circuit usable in the meter of the invention.

Suitable circuits usable in the meter of the invention are known in the art, for example from US Patent Publication No. US 2005-0265094 A1, which is incorporated herein by reference. One such circuit is shown in FIG. 9. In FIG. 9, an ideal voltmeter 942 is provided which can measure the potential across the electrodes 941, 938. Switch 944 is provided which is opened when the potential is to be measured or closed for measurement of current. When ope, the cell 939 is "floating" as to at least one of its electrodes, permitting a voltage measurement that is unaffected by signals at the amplifier 935. The switch 944 may be a mechanical switch (e.g. a relay) or an FET (field-effect transistor) switch, or a solid-state switch. In a simple case the switch opens to an open circuit; more generally it could open to a very high resistance.

This circuit can be used to measure either a potential difference or a current difference. As will be appreciated by persons skilled in the art, other circuits, including much simpler and more complicated circuits can be used to achieve application of either or both of a potential difference or a current.

The circuit of FIG. 9 can also be used to apply a potential difference to the test device of the invention. While, as discussed above, such application of potential is not required to perform the measurement of the invention, application of potential prior to the measurement (particularly in a test device with facing electrode construction) can result in a more rapid measurement time by effectively driving analyte and/or analyte-binding enzyme component towards the electrode with the immobilized reagent using what is in essence electrophoresis, provided that the analyte or analyte-binding enzyme component is charged under the conditions (particularly pH) found within the test device. A step function or a sine wave passing from negative to positive potential differences could also effect something similar to washing in situ within the test device.

VI. Advantages of the Invention

The present invention provides the ability to perform binding assays for the detection of analyte with electrochemical detection, without the need to apply an external potential or current, and without the need for washing steps commonly employed in sandwich immunoassay procedures. Because of this, the apparatus used to perform the assay can be much simpler, easy to use, and less expensive. In addition, the device components in an electrochemical assay are more robust than those used for example in optical measurements, facilitating the manufacture of the low cost reusable meter for use with disposable test devices.

The present invention can make use of small samples of blood, tears, saliva, or sweat, with minimal invasiveness to the subject. (samples of less than 10 ul, preferably less than 1 ul are particularly desirable for blood tests). Further, the present invention can provide for very rapid test times. Common immunoassay procedures take up to an hour or more. The small volume of the test devices of the invention and the sensitivity of the test to small differences in the distribution of the enzyme means that shorter times (for example less the 30 minutes, more preferably less than 10 minutes, and most preferably less than 1 minute) are accessible depending on the concentration of analyte to be measured and the binding kinetics of the analyte with the binding elements of the mobile and immobilized reagents.

Depending on the nature of the sample and the redox substrate, it may be possible to use materials from the sample as part of the reaction system. For example, endogenous glucose can be used as a component of the redox substrate in a glucose oxidase-based system when the sample is a blood sample.

EXAMPLES

In the following examples, the utility and operability of the invention are demonstrated using a model system in which enzyme is coated onto the surface of one of two electrodes in an electrode pair. This model does not require the capture of the enzyme, and therefore is useful for modeling the after-capture behavior with a limited number of variables, although it does not provide a full picture of the binding kinetics of an actual test system. Capture of enzyme using reagents in other enzyme sandwich, competition and displacement assays and the like is well known.

Example 1

Figure 10:
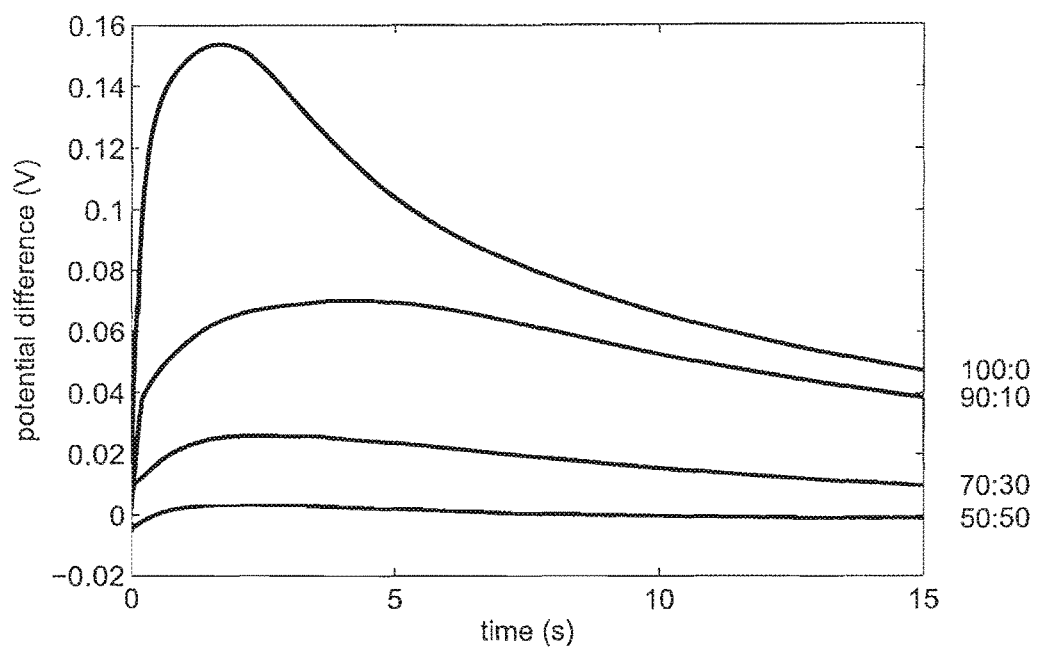
FIG. 10 shows potential difference in open circuit as a function of time for different levels of asymmetry in enzyme distribution between two electrodes.
Figure 11:
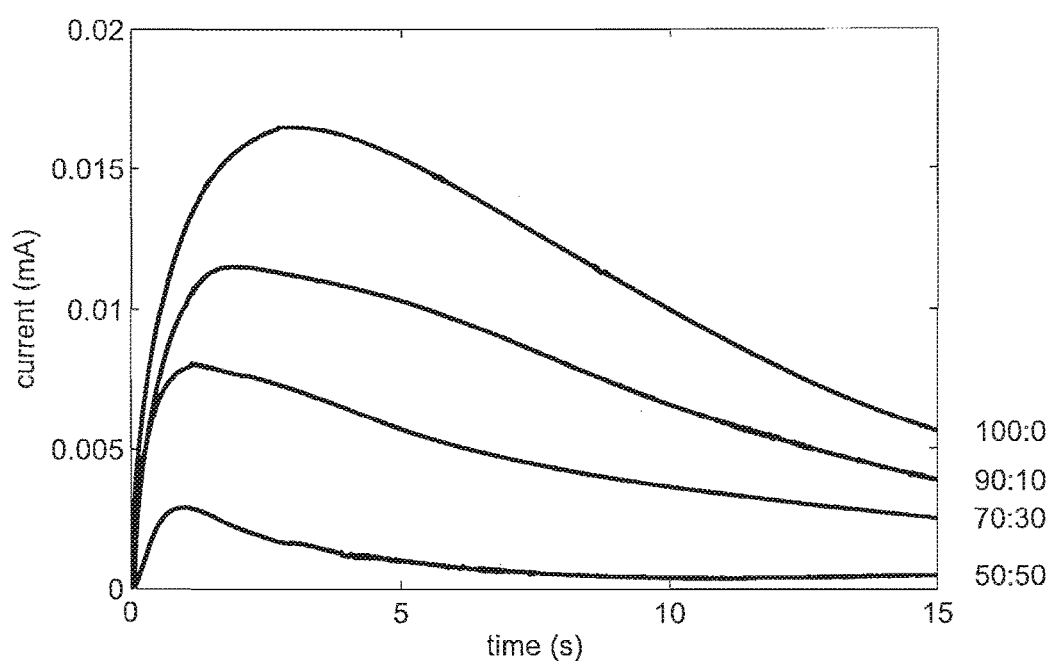
FIG. 11 shows current in short circuit as a function of time for different levels of asymmetry in enzyme distribution between two electrodes.

An electrochemical cell test strip comprising two gold electrodes separated by a double-sided adhesive layer was constructed using the method described in US Patent Publication No. US-2005-0258035-A1 which is incorporated herein by reference. An total of 100 nL enzyme solution (27 mg/mL, glucose oxidase in 100 mM sodium citrate buffer pH 4.1) was dispensed onto the two electrodes and allowed to dry. Test strips were made with different ratios of electrode enzyme activity by apportioning the 100 nL enzyme solution between the two electrodes, with the balance made up with water. For example to make strips with 75% enzyme activity on electrode 1 and 25% enzyme activity on electrode 2, 100 nL of a mixture of 3 parts enzyme solution to 1 part water was dispensed onto electrode 1, and 100 nL of a mixture of 1 part enzyme solution to 3 parts water was dispensed onto electrode 2. A solution of 100 mM—beta-D-glucose and 100 mM potassium ferricyanide in water was added to the electrochemical cell. The potential difference in open circuit (FIG. 10), or current in short circuit (FIG. 11), was recorded. It is noted that the period of time required to achieve clear differences in the signal at the different levels of asymmetry is short (less than 15 seconds) thus making the invention suitable for rapid measurement.

Figure 12:
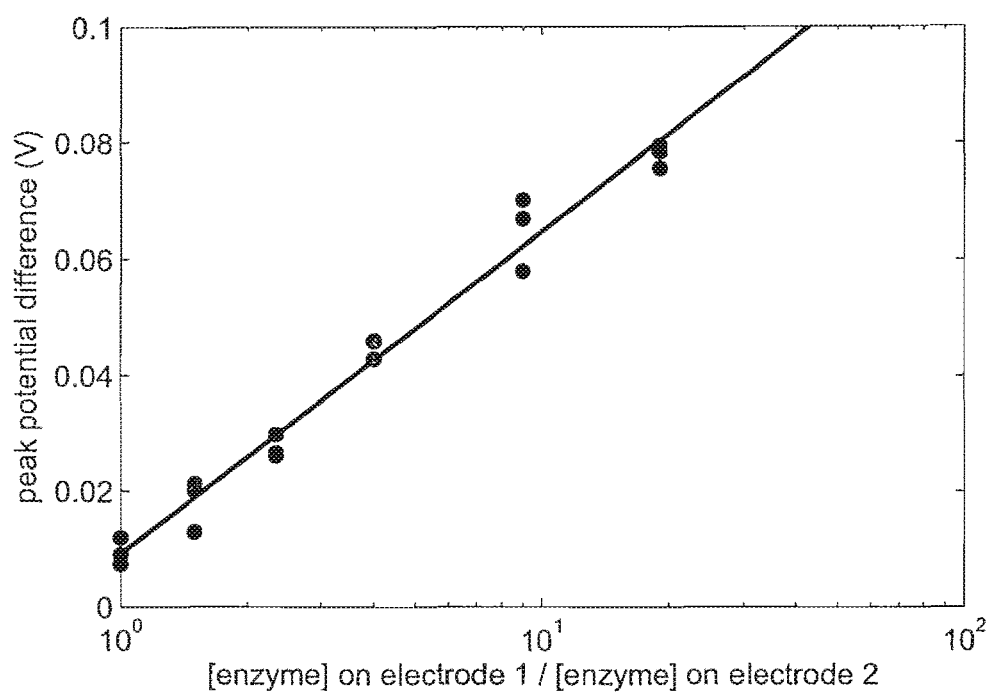
FIG. 12 shows the correlation of peak potential difference with ratio of electrode enzyme activities
Figure 13:
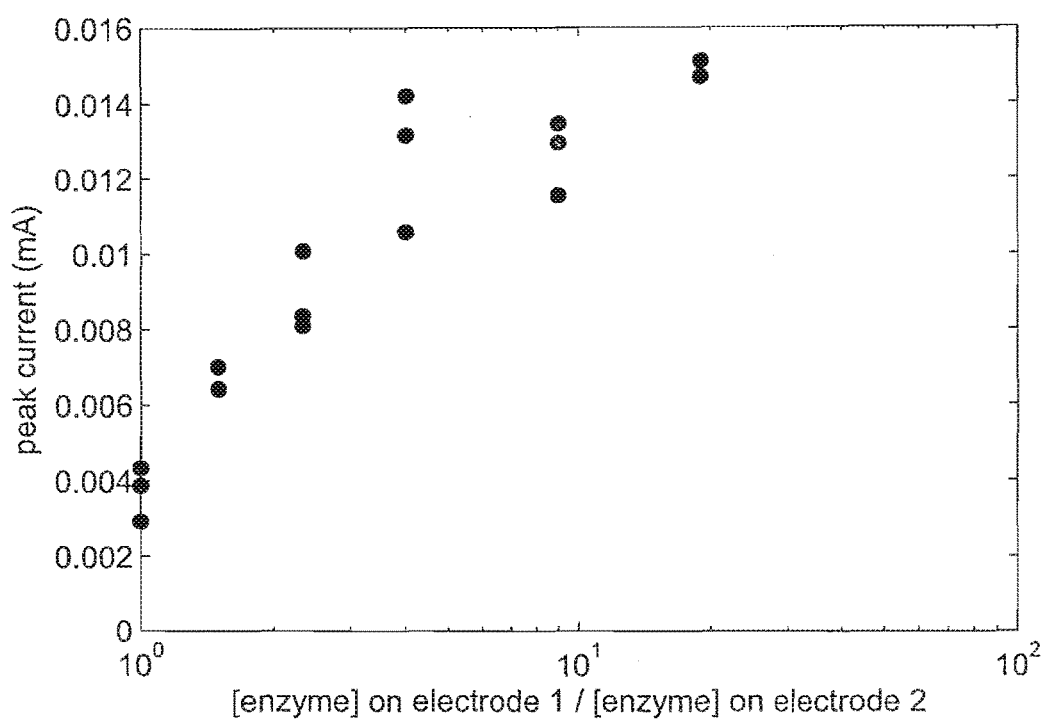
FIG. 13 shows the correlation of peak current with ratio of electrode enzyme activities

FIG. 12 shows that peak potential difference attained correlated with the ratio of enzyme activity dispensed on each electrode. FIG. 13 shows that peak current attained correlated with the ratio of enzyme activity dispensed on each electrode.

Example 2

By combining the determination of the ratio of enzyme activity dispensed on each electrode (as in Example 1) with a determination of total enzyme activity, the amount of enzyme (E1) present at one electrode can be determined independent of the amount (E2) present at the other electrode.

Varying amounts of enzyme were dispensed on 2 surfaces that served as electrodes in a sandwich configuration as described in Example 1. Ratio of enzyme activity present at the two electrodes (R=E1/E2) was determined by measurement of the current flowing in a short circuit configuration. Then the total enzyme activity ($E_t$=E1+E2) was determined by measuring the current flowing with an applied potential difference. E1 and E2 were then calculated from the determined values of R and E.

Test strips containing a range of 0.25 microgram to 1 microgram of glucose oxidase were made, with the enzyme distributed between the two electrodes such that R was between 1.5 and 19. These strips were made by dispensing a solution of 0.25 microgram to 1 microgram glucose oxidase in 100 nL of 100 mM sodium citrate buffer pH 4.1 onto electrode 1, and a solution of 0 to 0.4 microgram glucose oxidase in 100 nL of 100 mM sodium citrate buffer pH 4.1 onto electrode 2, then allowing the dispensed solutions to dry.

A solution of 100 mM beta-D-glucose and 100 mM potassium ferricyanide in water was added to the electrochemical cell and current in short circuit was recorded for 5 seconds. Following this, 300 mV was applied for 10 s. The current immediately prior to 5 s was averaged to give $I_0$ and the current immediately prior to 15 s was averaged to give $I_{300}$ (i.e. the measured I at 5 s is $I_0$ and measured I at 15 s was designated as $I_{300}$).

Measured I (both $I_0$ and $I_{300}$) for increasing amounts of $E_t$ each with a variable ratio R, was recorded and plotted.

Figure 14:
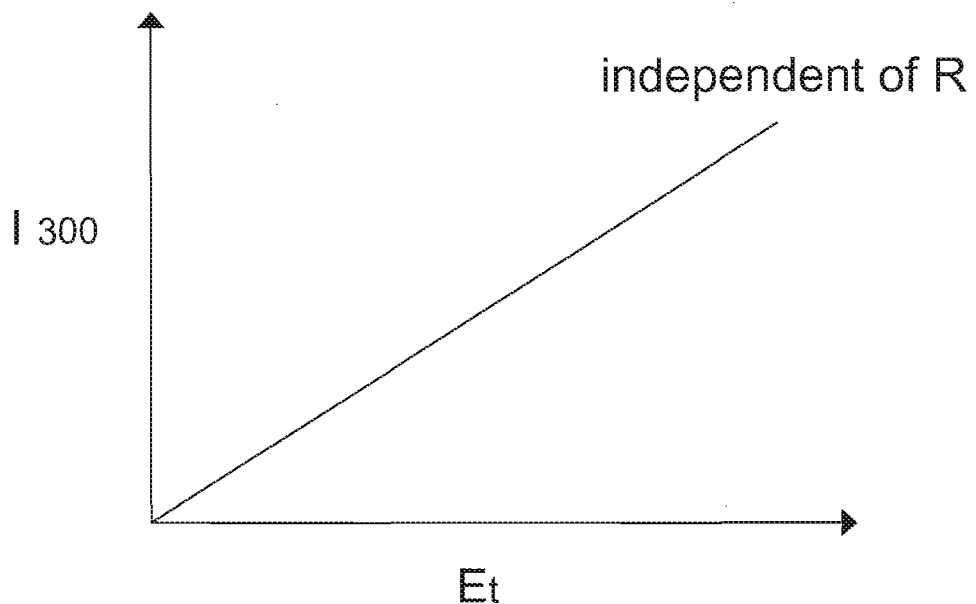
FIG. 14 shows a schematic plot of a known total enzyme $E_t$ on x-axis and measured $I_{300}$ on the y-axis.

FIG. 14 shows a schematic of known total enzyme $E_t$ on the x-axis and measured $I_{300}$ on the y-axis. The relationship between $E_t$ and $I_{300}$ can be established from this plot, for example the data can be represented by the equation $$I_{300}=m \times E_t + n$$

where m and n are the slope and intercept of the line.

Figure 15:
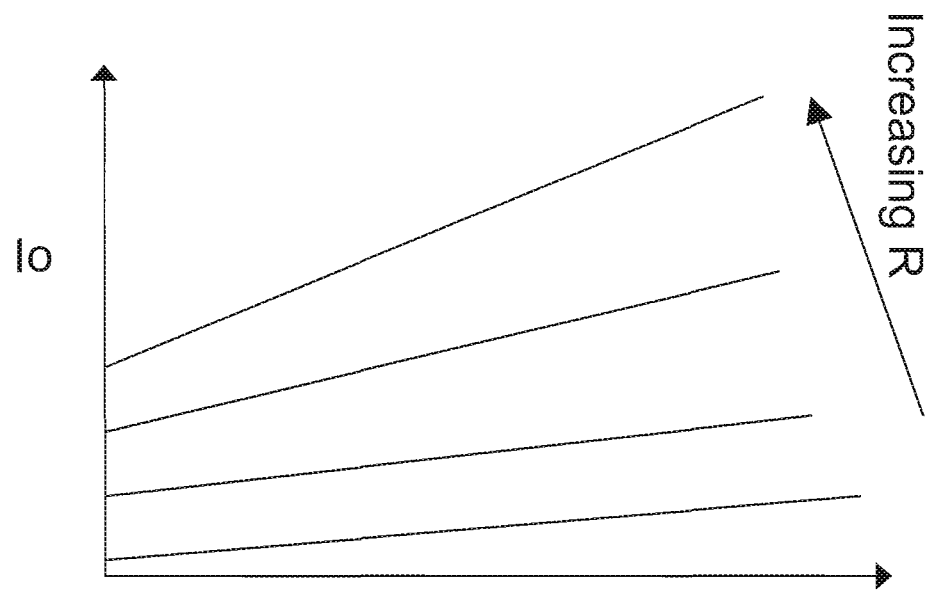
FIG. 15 shows a schematic plot of a known $E_t$ on x-axis and measured $I_0$ on the y-axis.

FIG. 15 shows a schematic plot of a known $E_t$ on x-axis and measured $I_0$ on the y-axis. As shown, a family of lines is generated, one for each value of the ratio R. From FIG. 15, the linear relationship of the $I_0$ current vs $E_t$ is dependent on R, ie $$I_0 = f(E_t, \log R)$$

To further establish this function, we plotted known log (R) vs slope (FIG. 16) for each line shown in FIG. 15. In addition, as shown in FIG. 17 we plotted known log (R) and intercept for each line in FIG. 15.

Thus the function f can further be defined as the relationship $$I_0 = (a \log R + b) \times E_t + (c \log R + d)$$

Figure 16:
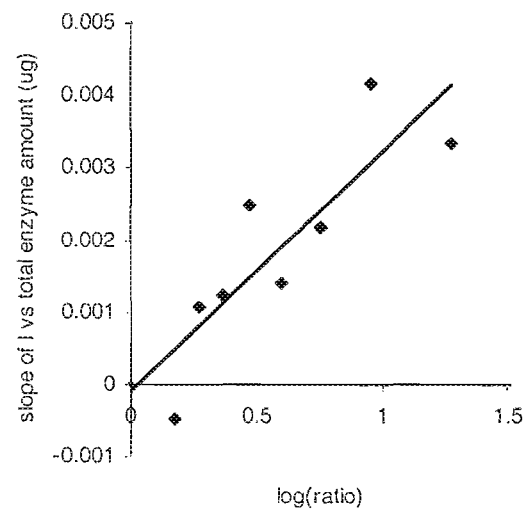
FIG. 16 shows a plot of how log (R) affects the slope of $I_0$ versus $E_t$ which is used to derive parameters a and b.
Figure 17:
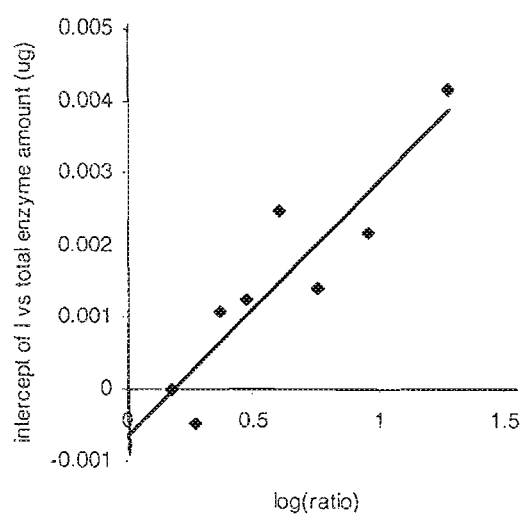
FIG. 17 shows a plot of log (R) affects the intercept of $I_0$ versus $E_t$ which is used to derive parameters c and d.

The parameters a and b can be calculated from the plots in FIG. 16 and the parameters c and d from FIG. 17. Once the parameters a, b, c, d, m and n have been determined, E1 can be calculated as follows:

1. Calculate $E_t$ from $I_{300}$ $$E_t = (I_{300} - n) \div m.$$

2. Calculate R from $I_0$ and $E_t$ $$\log R = (I_0 - b \times E_t - d) \div (a \times E_t + c)$$

$$R = 10^{\log R}$$

3. Calculate $E_1$ from $E_t$ and R $$E_1 = (R \times E_t) \div (1 + R)$$

Figure 18:
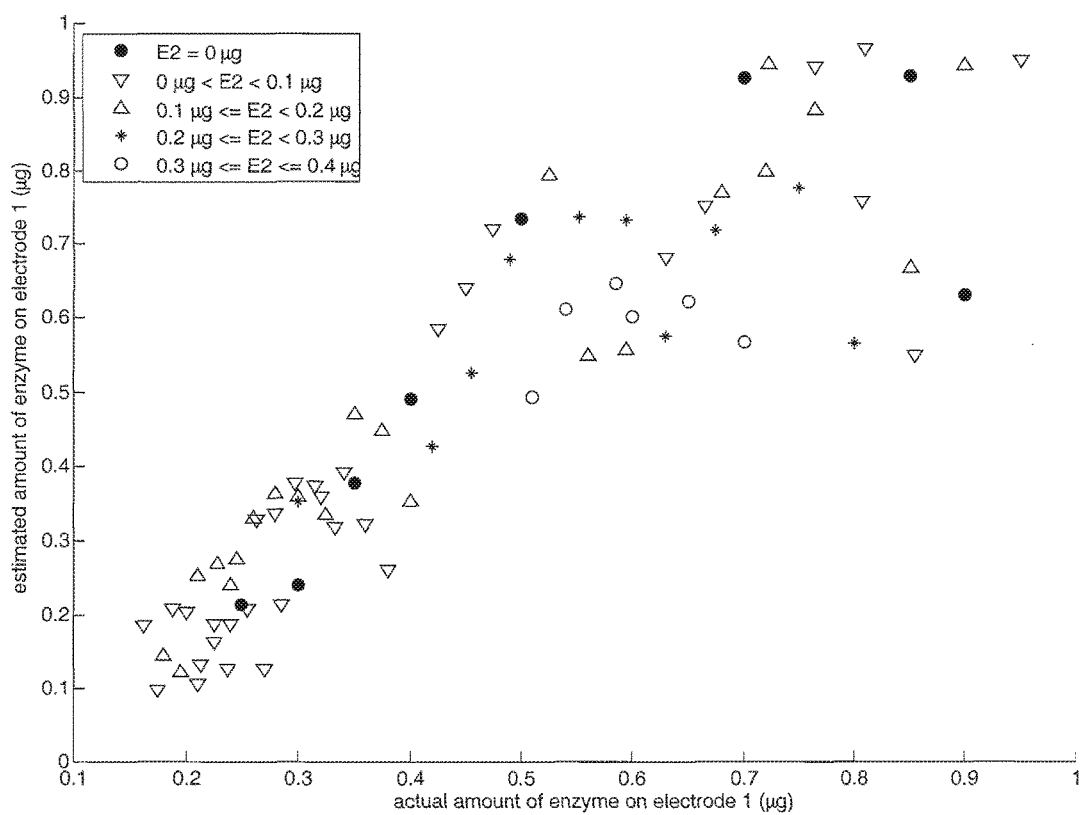
FIG. 18 shows the correlation between the actual amount of an enzyme and the estimated amount of enzyme as determined in accordance with the invention.

FIG. 18 shows calculated values of $E_1$ versus actual values of $E_1$, for strips with varying amounts of enzyme on the two electrodes. FIG. 18 indicates that our estimated values for the enzyme dispensed on one electrode correlated well with the actual amount that was dispensed, and were independent of the amount of enzyme dispensed on the other electrode.

What is claimed is:

1. A method for determining the amount of enzyme present at one electrode independent of the amount of enzyme present at a second electrode, comprising the steps of:
   (a) introducing a sample to a test cell comprising first and second electrodes, a mobile test reagent comprising a redox enzyme portion, and reagents that interact with the mobile test reagent and/or the analyte, such that the mobile test reagent has a first distribution relative to the electrodes when analyte is present in the sample and a second distribution relative to the electrodes when analyte is not present sample, one of said first and second distributions being asymmetric with respect to a line between the electrodes, and the other of the first and second distributions being symmetric or less asymmetric with respect to the line between the electrodes,
   (b) supplying a redox substrate for the redox enzyme in the test cell, said redox substrate being acted upon by the redox enzyme to produce a chemical potential gradient between the first and second electrodes, wherein the magnitude of the chemical potential gradient is determined by the distribution of the mobile test reagent and thus on the presence of analyte,
   (c) detecting the chemical potential gradient, $I_0$, between the first and second electrodes to determine the ratio of enzyme activity present at the two electrodes, wherein the formation and detection of the chemical potential gradient are performed without application of an external potential or current,
   (d) applying a potential and measuring the resulting current, $I_{300}$, between the first and second electrodes, and
   (e) calculating an amount of enzyme, $E_1$, present at one electrode.

2. The method of claim 1, wherein the test cell comprises as one of the reagents that interact with the analyte an immobilized test reagent disposed on the surface of the first electrode, said immobilized test reagent comprising an analyte binding portion, and the mobile test reagent comprises an analyte-binding portion and the redox enzyme portion, whereby if analyte is present in the sample in the test cell, at least a portion of the mobile test reagent becomes immobilized on the first electrode thereby creating an asymmetric distribution of redox enzyme concentration between the first and second electrodes when analyte is present.

3. The method of claim 2, wherein the analyte binding portion of the immobilized test reagent and the analyte are an antibody-antigen pair or antibody/hapten pair.

4. The method of claim 3, wherein the redox enzyme and the redox substrate comprises glucose and a mediator compound.

5. The method of claim 2, wherein the analyte binding portion of the immobilized test reagent is a drug receptor.

6. The method of claim 5, wherein the redox enzyme and the redox substrate comprises glucose and a mediator compound.

7. The method of claim 2, wherein the analyte binding portion of the immobilized test reagent is a hormone receptor.

8. The method of claim 7, wherein the redox enzyme and the redox substrate comprises glucose and a mediator compound.

9. The method of claim 1, wherein the analyte binding portion of the immobilized test reagent and the analyte are an antibody-antigen pair or antibody/hapten pair.

10. The method of claim 9, wherein the redox enzyme and the redox substrate comprises glucose and a mediator compound.

11. The method of claim 1 wherein the analyte binding portion of the immobilized test reagent is a drug receptor.

12. The method of claim 11, wherein the redox enzyme and the redox substrate comprises glucose and a mediator compound.

13. The method of claim 1, wherein the analyte binding portion of the immobilized test reagent is a hormone receptor.

14. The method of claim 13, wherein the redox enzyme and the redox substrate comprises glucose and a mediator compound.

15. The method of claim 1, wherein $E1=(R \times E_t+R)$, where R is the ratio of enzyme activity present at the two electrodes, $E_t$ is the total enzyme activity.

* * * * *

UNITED STATES PATENT AND TRADEMARK OFFICE
CERTIFICATE OF CORRECTION

PATENT NO. : 9,939,440 B2
APPLICATION NO. : 15/017787
DATED : April 10, 2018
INVENTOR(S) : Harding et al.

It is certified that error appears in the above-identified patent and that said Letters Patent is hereby corrected as shown below:

In the Claims

In Column 12, Lines 24-35, Claim 1 should be: --- (a) introducing a sample to a test cell comprising first and second electrodes, a mobile test reagent comprising a redox enzyme portion, and reagents that interact with the mobile test reagent and/or the analyte, such that the mobile test reagent has a first distribution relative to the electrodes when analyte is present in the sample and a second distribution relative to the electrodes when analyte is not present in the sample, one of said first and second distributions being asymmetric with respect to a line between the electrodes, and the other of the first and second distributions being symmetric or less asymmetric with respect to the line between the electrodes, ---

Signed and Sealed this
Twenty-second Day of May, 2018

Andrei Iancu
*Director of the United States Patent and Trademark Office*